United States Patent [19]

MacGregor

[11] 4,280,514
[45] Jul. 28, 1981

[54] ENDOCARDIAL PACEMAKER ELECTRODE

[76] Inventor: David C. MacGregor, 81 Wimbleton Rd., Islington, Ontario, Canada

[21] Appl. No.: 59,786

[22] Filed: Jul. 23, 1979

Related U.S. Application Data

[63] Continuation-in-part of Ser. No. 824,296, Aug. 15, 1977, which is a continuation-in-part of Ser. No. 683,382, May 5, 1976, Pat. No. 4,101,984.

[51] Int. Cl.³ .............................................. A61N 1/04
[52] U.S. Cl. .................................. 128/786; 128/419 P
[58] Field of Search .............................. 128/784–786, 128/419 P

[56] References Cited

U.S. PATENT DOCUMENTS

| 3,871,382 | 3/1975 | Mann | 128/419 P |
|---|---|---|---|
| 3,981,309 | 9/1976 | Cannon | 128/786 |
| 4,033,357 | 7/1977 | Helland et al. | 128/785 |
| 4,052,754 | 10/1977 | Homsy | 128/784 |
| 4,156,429 | 5/1979 | Amundson | 128/419 P |

Primary Examiner—William E. Kamm
Attorney, Agent, or Firm—Sim & McBurney

[57] ABSTRACT

An endocardial pacemaker electrode is constructed of electroconductive metal inert to blood and consists of a dense rigid metal substrate and a rigid porous metal coating adhered to at least a major portion of the substrate. The electrode has a regular geometrical shape with a maximum transverse dimension of about 0.5 to 3 mm and a minimum longitudinal dimension of at least about 0.25 mm. The porous coating includes a plurality of metal particles bonded together at their points of contact with each other and with the substrate to form a network of interconnected pores substantially uniformly distributed throughout the coating. The porous coating has a porosity of about 10 to 50% by volume and a thickness of less than about 500 microns. The metal particles have a particle size selected from −100 +325 mesh, −325 +500 mesh and −500 mesh. The porous coating permits tissue formation from cellular elements in the blood stream to stabilize its position in the heart and the formation of surface tissue in those areas exposed to flowing blood prevents the formation of blood clots.

14 Claims, 11 Drawing Figures

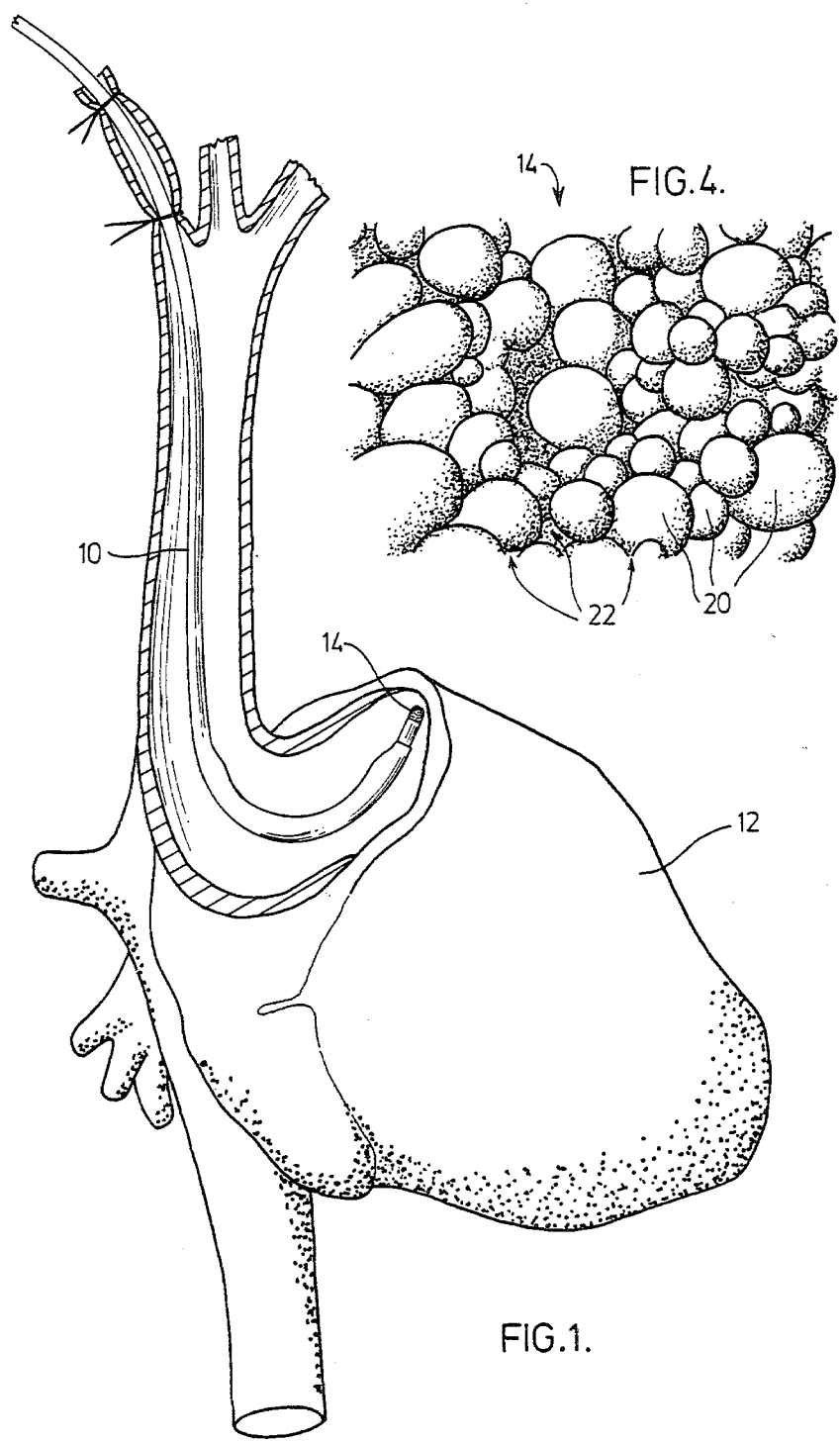

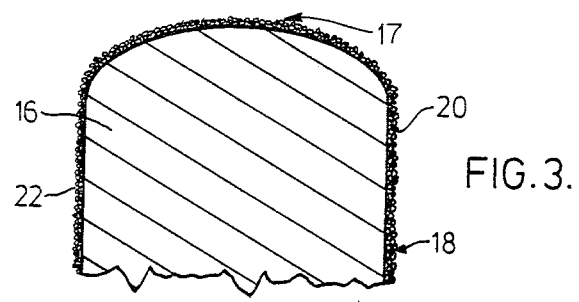
FIG. 3.
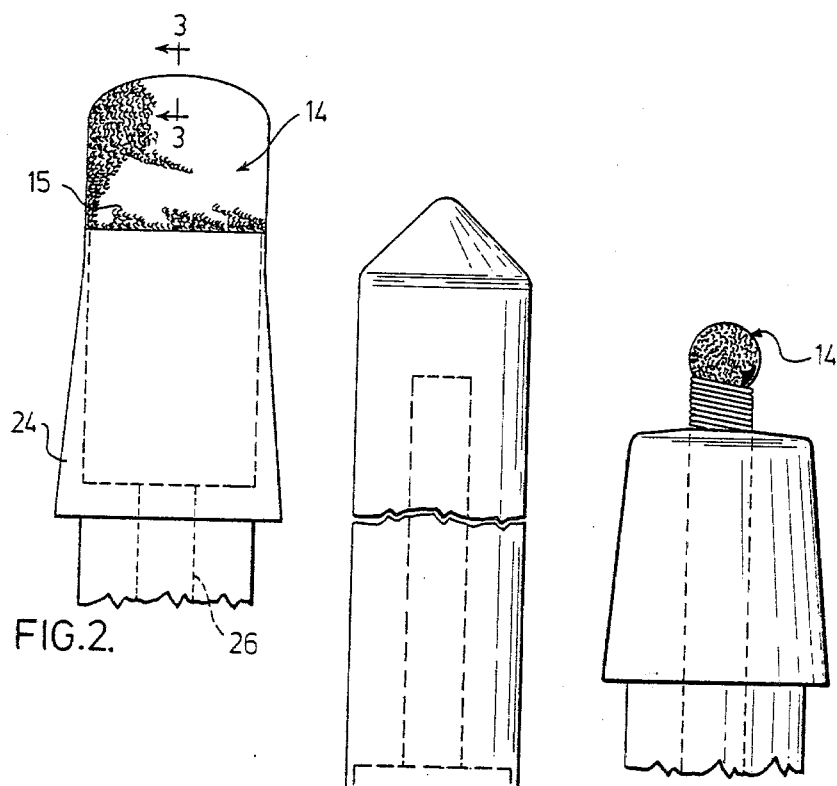
FIG. 2.
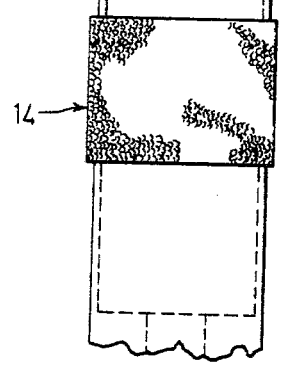
FIG. 7.
FIG. 8.

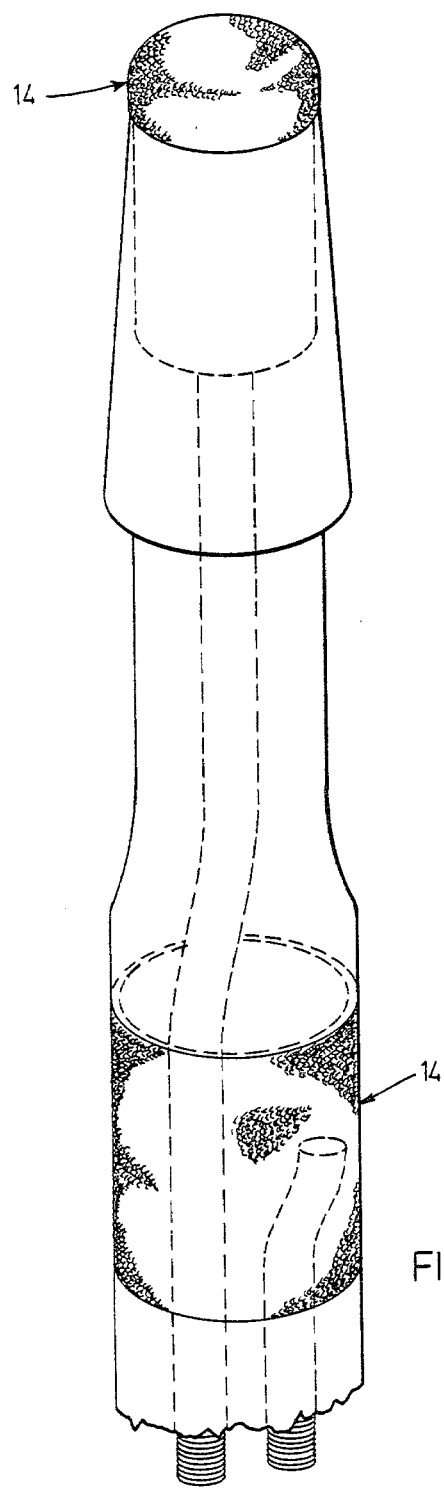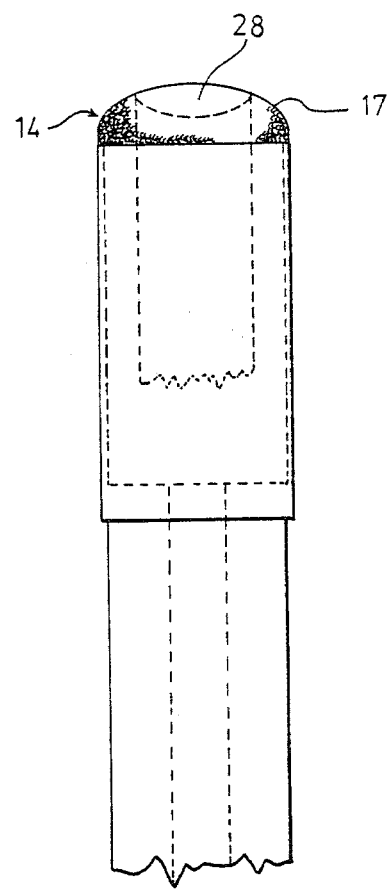

4,280,514

ENDOCARDIAL PACEMAKER ELECTRODE

REFERENCE TO RELATED APPLICATIONS

This application is a continuation-in-part of copending U.S. application Ser. No. 824,296 filed Aug. 15, 1977 which itself is a continuation-in-part of U.S. application Ser. No. 683,382 filed May 5, 1976, now U.S. Pat. No. 4,101,984.

FIELD OF INVENTION

This invention relates to endocardial pacemaker electrodes.

BACKGROUND TO THE INVENTION

Three major problems which may be encountered with endocardial pacemaker electrodes are a lack of stable position, a chronic increase in stimulation threshold and a diminishing magnitude of the sensed endocardial signal during use. These problems are particularly manifest in the atrium, where the maintenance of a stable anatomical position of the electrode has been a particularly difficult problem in the development of satisfactory endocardial leads for atrial pacing.

Another problem which is manifested in the blood stream by polished metal surfaces, such as are typically used in pacemaker electrodes, is the tendency to cause the formation of blood clots which may break loose and embolize to various parts of the body.

SUMMARY OF INVENTION

In accordance with the present invention, there is provided an endocardial heart pacemaker electrode having a porous surface of specific dimensions to permit tissue to form in the pores and at the surface thereof with a resulting tissue bond to the adjacent endocardium, thereby achieving a stable position of the electrode tip. In addition, the tissue formed at the surface provides a thin tissue covering on the exposed surface to render the same resistant to the formation of blood clots.

The fixation of the electrode in the atrium by tissue formation overcomes the problems of maintenance of a stable anatomical position characteristic of the prior art and enables low stimulation thresholds and a consistent magnitude of the sensed endocardial signal to be maintained.

The formation of the tissue coating on the exposed portions of the electrode surface with the consequent resistance of the surface to the formation of blood clots overcomes another difficulty of the prior art.

The electrode of the present invention is primarily designed for endocardial use for atrial pacemaking and is described with particular reference thereto. The electrode of the present invention, however, may also be used for endocardial ventricular or coronary sinus pacing.

BRIEF DESCRIPTION OF DRAWINGS

FIG. 1 is a diagrammatic view of a heart having an endocardial pacemaker lead extending therein with the electrode positioned in the atrium in contact with endocardium;

FIG. 2 is a close-up perspective view of the electrode used in the endocardial pacemaker lead of FIG. 1;

FIG. 3 is a sectional view of the electrode taken on line III—III of FIG. 2;

FIG. 4 is an extreme close-up view of the porous coating of the electrode;

FIGS. 6 to 9 illustrate alternative endocardial electrode geometrical configurations.

DESCRIPTION OF PREFERRED EMBODIMENT

Figure 5:
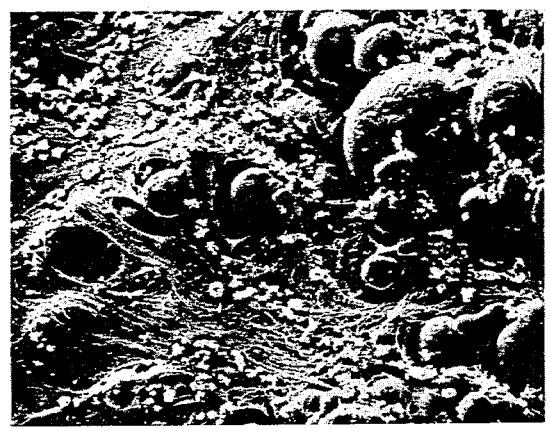
FIG. 5 is a scanning electron micrograph illustrating the tissue which forms in the porous coating of the electrode.

Referring to FIGS. 1 to 4, there is illustrated an endocardial pacemaker lead 10 positioned in a heart 12 with the electrode 14 located at the apex of the right atrial appendage of the heart 12. The electrode 14 has a generally cylindrical body 15 with a partly rounded end 17. This lead 10 is of conventional construction, except that the electrode 14 is differently structured, as compared with conventional smooth surfaced metal electrodes. The electrode 14, constructed in accordance with this invention, consists of a dense coherent metal substrate 16 and a porous metal coating 18 thereover.

The coating 18 is formed from a plurality of metal particles 20 which are bonded together at their points of contact with each other and with the substrate to form a network of interconnected pores 22 substantially uniformly distributed throughout the coating 18.

The overall length of the electrode 14 protruding from the end of the lead 10 for engagement with the endocardium is about 1 to about 3 mm, preferably about 2 mm, and its diameter is also about 1 to about 3 mm, preferably about 2 mm.

The metal particles 20 in the coating 18 are generally made up of a mixture of particles of varying particle sizes within one of three narrow ranges of particle size, namely $-100 +325$ mesh, $-325 +500$ mesh and $-500$ mesh.

The thickness of the coating 18 may vary widely, depending on the size of the particles 20 and the number of layers of particles desired in the coating, up to about 500 microns. A thickness in the range of about 100 to about 300 microns is preferred for the larger size particles and a thickness in the range of about 20 to about 150 microns is preferred for the smaller size particles.

The coating 18 has a porosity of about 10 to about 50% by volume, and coating 18 and the interface of the coating 18 and the substrate 16 usually have a shear strength of greater than about 1000 psi to ensure adequate structural strength.

The end of the porous metal coating 18 remote from the rounded end 17 may be utilized to bond the polymer sleeve 24 surrounding the current conducting wire 26 of the lead 10 to the electrode tip 14. This bonding may be achieved by causing the sleeve polymer to flow into the porous metal surface and harden in the subsurface pores 22 to interlock the sleeve 24 with the coating 18, for example, by pressure molding.

The engagement of the porous coating 18 with the bloodstream in the atrium results in a controlled thrombotic reaction in which blood elements, including erythrocytes, platelets and leukocytes, accumulate in the pore network 22 and on the surface of the porous metal coating. Subsequent organization of this thrombus tissue, when in contact with the endocardium, results in the development of fibrous tissue within the pore network 22 and on the surface of the porous coating 18 with a resulting tissue bond to the adjacent endocardium. This fibrous tissue is formed by colonization of nucleated cells circulating in the bloodstream onto the exposed porous coating 18 and subsequent differentiation into other cell types which include fibrocytes. In the scanning electron micrograph of FIG. 5, the appearance of the mature collagen tissue is shown with collagen bundles in the interstices between the metal spheres.

The exposed portions of the porous coating 18 not in contact with the endocardium promotes the formation of a smooth, thin, adherent tissue covering on the porous surface, thereby rendering the same resistant to the formation of blood clots. The tissue coating is formed rapidly over a one to three month period and does not appear to increase significantly in thickness thereafter. This tissue response also represents organization of thrombus resulting in fibrous tissue formation within the pore network and on the surface of the porous coating 18 but the blood-contacting tissue surface consists of flattened endothelial-like cells which confer thromboresistance. An example of this type of tissue coating may be seen in FIG. 6 of the aforementioned U.S. Pat. No. 4,101,984.

The formation of the fibrous tissue in the porous coating of the electrode 14 with the consequent tissue bond to the endocardium fixedly locates the same in close proximity to the underlying myocytes, enabling consistently low chronic stimulation thresholds and a consistent magnitude of the sensed endocardial signal to be maintained.

The latter results contrast markedly with conventional leads which have smooth metal tips. The lack of stable fixation to the endocardium causes a tissue reaction and the formation of a thick tissue layer on the endocardium, widely separating the electrode from the myocardium, thereby causing an increase in stimulation threshold and decreased sensed endocardial signal during use.

DESCRIPTION OF ALTERNATIVE EMBODIMENTS

Turning now to FIGS. 6 to 9, these Figures illustrate alternative endocardial electrode geometrical configurations, which may be used in place of the electrode 14.

FIG. 6 illustrates the same geometrical shape of tip as electrode 14 in FIGS. 2 and 3, except that in this instance the end 17 contains an insulating plug. This arrangement decreases the overall surface area of the electrode by the extent of the insulation, and is desirable in certain instances. The permissible range of transverse dimension is the same as that for the electrode 14 of FIGS. 2 to 4, whereas the range of longitudinal dimensions is about 0.25 to about 1.5 mm. The diameter of the insulating plug 28 may vary widely. For example, the insulating plug 28 may have a diameter of about 0.5 to about 1.5 mm.

The electrode illustrated in FIG. 7 is generally spherical in shape, with a diameter of about 0.5 to about 2 mm, preferably about 1 mm. The electrodes illustrated in FIGS. 2 to 6 act as tips to the lead.

FIGS. 8 and 9 illustrate leads using a thin cylindrical electrode sleeve which is positioned remote from the end of the lead, and may be used alone (as in the case of FIG. 8) or in combination with a tip electrode of one of the types shown in FIGS. 2 to 5 and 7 (as in the case of FIG. 9), depending on the intended use of the lead.

The electrode sleeve has an outside diameter of about 1 to about 3 mm, preferably about 2 mm, a thin wall usually of thickness of about 0.05 to about 0.3 mm, and a length of about 1 to about 10 mm, preferably about 3 mm.

EXAMPLE

Twenty-four pacemaker electrodes were formed of the alloy "ELGILOY" (Trademark), each having a diameter of 2.3 mm and a length of 2.3 mm.

Six of the electrodes (Group IV) were porous metal coated with a particle size fraction in which all particles were 20 microns or less in diameter. Twelve of the electrodes (Groups II and III, 6 each) were porous metal coated with a particle size fraction of 20 to 50 microns. The remaining six electrodes (Group I) were uncoated and served as controls.

The electrodes were machined down prior to coating so that the coated electrodes had an overall diameter which is the same as the six uncoated electrodes. The thickness of the coating in each case was about 100 microns. All twenty-four electrodes were incorporated into J-shaped atrial pacemaker leads.

The eighteen porous coated atrial pacemaker electrodes as well as the six uncoated pacemaker electrodes were implanted in dogs. Each lead was introduced into the right atrial appendage through the right subclavian vein. The terminal pin of eighteen of the porous coated electrodes was connected to a fixed-rate pulse generator (modified "CORDIS" (Trademark) Model 162D) implanted subcutaneously in the anterior chest wall to provide for chronic stimulation at a rate of 60 beats per minute, a current of 8 to 9 milliamperes and a pulse-width of 2 milliseconds.

Under light general anaesthesia, measurements of stimulation threshold (constant current, 1 millisecond pulse-width), P-wave amplitude and source impedance were made for all the leads at the time of implant and immediately prior to explant. These measurements were made using a modified Cordis Model 209A Pacer Systems Analyzer and a resistive attenuator. The measurements were taken from the terminal pin of the lead plus a standard skin needle inserted into the subcutaneous tissue in the right mid flank region to serve as a ground electrode. For each parameter, the mean value and standard deviation (S.D.) were calculated for each group and the results compared using the t test for either paired or unpaired data. The level of significance chosen was $p < 0.05$.

At thirty weeks, all twenty-four dogs were sacrificed. The right atrium was opened to determine the presence or absence of fixation of the electrode and to observe the tissue reaction to it. The electrode was then removed and, if porous-surfaced (Groups II, III and IV), it was submitted for scanning electron microscopy to determine the presence and nature of tissue ingrowth into the pores. In Groups III and IV, the force required to dislodge each porous-surfaced electrode was determined under controlled conditions (rate of loading of 100 g per minute) prior to submitting the electrode for scanning electron microscopy (SEM). The site of contact between the electrode and the endocardium was excised from each heart for light microscopic examination.

A comparison of the stimulation threshold performance results obtained at implant and explant is set forth in the following Table I:

TABLE I

STIMULATION THRESHOLD PERFORMANCE

| Group and Comparison | Particle size Distribution | Chronic Pacing | Threshold* Implant | (milliamperes) Explant |
|---|---|---|---|---|
| I | No coating | No | 0.82 ± 0.39 | 6.1 ± 1.8 |
| I vs II | | | NS | p<0.001 |
| II | 20–50 microns | No | 0.77 ± 0.18 | 1.7 ± 0.62 |
| II vs III | | | NS | NS |
| III | 20–50 microns | Yes | 1.10 ± 0.31 | 1.30 ± 0.37 |
| III vs IV | | | NS | NS |
| IV | 20 microns and less | Yes | 1.10 ± 0.30 | 1.18 ± 0.22 |

*Constant current stimulation, 1 millisecond pulse duration. All values are mean ± standard deviation. Statistical analysis is by t test for unpaired data, the level of significance chosen being p<0.05.
NS = not significant.

As may be seen from the results reproduced in Table I, there was no significant difference between the thresholds at implantation of any two groups. At explantation, the mean thresholds of all groups of porous surfaced electrodes showed relatively little change from the time of implantation in marked contrast to the very large increase in mean chronic threshold observed in the smooth surfaced controls (Group I). Chronic pacing did not make a significant difference to the explant thresholds of identical porous surfaced electrodes (Group II vs. Group III). Similarly, particle size, comparing the less than 20 micron fraction with the 20 to 50 micron fraction, did not make a significant difference to the explant thresholds of otherwise identical electrodes (Group III vs. Group IV).

Figures 10A, 10B:
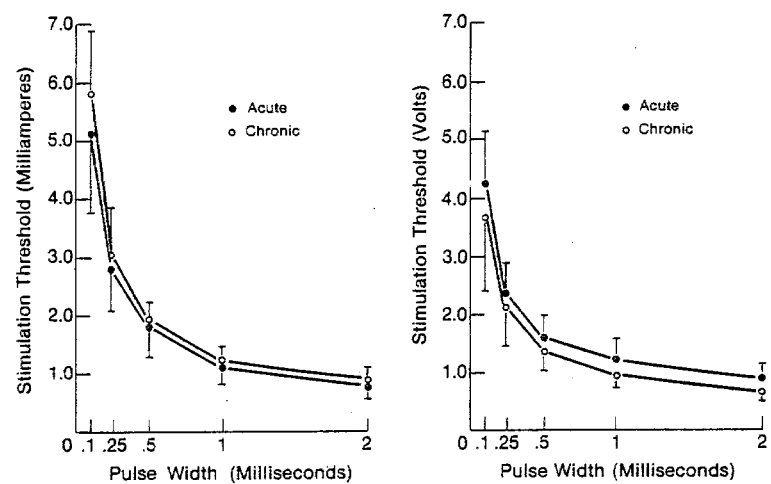
FIGS. 10A and 10B show representative strength-duration curves for stimulation thresholds of the porous-surfaced electrode when used in atrial pacing.

Strength duration curves for the porous-surfaced electrodes with the finer (20 microns or less) porous metal coating (Group IV), obtained under both constant current and constant voltage conditions at implant and explant (30 weeks), are plotted in FIG. 10. These plots indicate that for all pulse durations over the range of 0.1 to 2.0 milliseconds, there was no statistically significant increase (unpaired analysis) in chronic over acute thresholds for the porous-surfaced electrodes. The same conclusion was supported by the stimulation threshold data for the larger (20 to 50 microns) particle size coating (Group III). Paired statistical analysis also confirmed no significant increase in chronic versus acute thresholds in either Group III or Group IV over the 0.1 to 2.0 millisecond pulse width range.

The porous-surfaced electrodes also provided superior sensing performance compared with the smooth-surfaced controls. The sensed P-wave amplitude under acute and chronic conditions showed considerable dog to dog variability (range 3 to 9 millivolts) making unpaired compared comparisons inconclusive. However, paired analysis of the change in P-wave amplitude between acute and chronic (30 week) conditions revealed that all of the porous-surfaced electrodes provided a P-wave of equal or greater amplitude under chronic conditions with relative increases of 40% or greater in over half the cases. Whereas the porous-surfaced electrodes collectively (Groups II, III and IV) showed a highly significant (p<0.001) increase in sensed P-wave amplitude of +1.92±1.3 millivolts from acute to chronic conditions, the smooth-surfaced controls demonstrate no significant improvement in chronic P-wave sensing with a change of P-wave amplitude of −0.88±2.1 millivolts between acute and chronic conditions. In three of the six controls, there was a chronic decline of sensed P-wave amplitude of 30 to 40%. The porous surfaces also provided a chronic source impedence (0.71±0.11 kilo-ohms) which was significantly less (p<0.001) than that (1.4±0.28 kilo-ohms) of the controls.

The examinations and tests at explant referred to above showed that, in the case of the porous metal surfaced electrodes, stable tissue fixation to the endocardium at the apex of the right atrial appendage had occurred whereas, in the case of the control electrodes, no endocardal fixation had occurred and a build-up of pink tissue of granular consistency, more vascular than the surrounding normal-appearing endocardium and varying from 1 to 3 mm in thickness had formed.

The porous coated electrodes were lodged between trabeculae and left a shallow crater in the tissue surrounding it when removed. While each was definitely fixed to the endocardium, it was possible to remove the electrode with moderate traction. The strength of the bond between the porous-surfaced electrode and endocardium varied from 106 to 275 g and did not appear to be significantly influenced by either the particle size fraction of the porous coating.

Light microscopic examination of the tissue response to all of the porous surfaced electrodes revealed mature collagen-rich fibrous tissue surrounding the electrode and anchoring it in close proximity to the underlying myocardium so that the minimum distance between the electrode and the underlying myocytes was only about twice the thickness of the normal adjacent endocardium. In contrast, the tissue response to all of the control electrodes consisted of a thick build-up of tissue beneath the electrode to a thickness typically 7 to 15 times that of the normal endocardium.

SUMMARY OF DISCLOSURE

In summary of the disclosure of this application, the present invention relates to endocardial pacemaker electrodes having improved characteristics. Modifications are possible within the scope of the invention.

What I claim is:

1. An endocardial heart pacemaker electrode for endocardial atrial and ventricular pacing constructed of electroconductive metal inert to blood and consisting of a dense rigid metal substrate and a rigid porous metal coating adhered to at least a major portion of said substrate, said electrode having a regular geometrical shape, a maximum transverse dimension of about 0.5 to about 3 mm and a minimum longitudinal dimension of at least about 0.25 mm, said porous coating including a plurality of metal particles bonded together at their points of contact with each other and with said substrate to form a network of interconnected pores substantially uniformly distributed throughout the coating, said porous coating having a porosity of about 10 to about 50% by volume and a thickness of less than about 500 microns, said metal particles having a particle size selected from the group consisting of less than 100 mesh.

2. The electrode of claim 1 wherein said coating has a thickness of about 100 to about 300 microns.

3. The electrode of claim 2 wherein said coating has a thickness of about 20 to about 150 microns.

4. The electrode of claim 1, 2 or 3 wherein said regular geometrical shape is spherical and said transverse and longitudinal dimensions are about 0.5 to about 2 mm.

5. The electrode of claim 4 wherein said transverse and longitudinal dimensions are about 1 mm.

6. The electrode of claim 1, 2 or 3 wherein said regular geometrical shape is hollow cylindrical, said longitudinal dimension is about 1 to about 10 mm, and a wall thickness of about 0.05 to about 0.3 mm.

7. The electrode of claim 6 wherein said transverse dimension is about 2 mm and said longitudinal dimension is about 3 mm.

8. The electrode of claim 1, 2 or 3 wherein said regular geometrical shape includes an elongate cylindrical portion and an integral rounded end portion having an axially extending central portion therein filled with electrically-insulating inert polymeric material, said transverse dimension is about 1 to about 3 mm, said longitudinal dimension is about 0.25 to about 1.5 mm, and said central portion has a diameter of about 0.5 to about 1.5 mm.

9. The electrode of claim 8 wherein said transverse dimension is about 2 mm and said longitudinal dimension is about 0.5 mm.

10. An endocardial heart pacemaker electrode for endocardial atrial and ventricular pacing constructed of electroconductive metal inert to blood and consisting of a dense rigid metal substrate and a rigid porous metal coating adhered to at least a major portion of said substrate, said electrode having a regular geometrical shape including an elongate solid cylindrical portion and an integral rounded end portion, said electrode having transverse and longitudinal dimensions which are both about 1 to about 3 mm, said porous coating including a plurality of metal particles bonded together at their points of contact with each other and with said substrate to form a network of interconnected pores substantially uniformly distributed throughout the coating, said porous coating having a porosity of about 10 to about 50% by volume and a thickness of less than about 500 microns, said metal particles having a particle size of less than 100 mesh.

11. The electrode of claim 10 wherein said transverse and longitudinal dimensions are both about 2 mm.

12. The electrode of claim 1 or 8 wherein said metal particles have a particle size of −100 +325 mesh.

13. The electrode of claim 1 or 8 wherein said metal particles have a particle size of −325 +500 mesh.

14. The electrode of claim 1 or 8 wherein said metal particles have a particle size of −500 mesh.

* * * * *